United States Patent [19]

Isaacs

[11] Patent Number: 5,002,658
[45] Date of Patent: Mar. 26, 1991

[54] WATER PURIFICATION DEVICE AND METHOD

[76] Inventor: Bruce Isaacs, 5290 Alvahs La., Cutchoque, N.Y. 11935

[21] Appl. No.: 441,758

[22] Filed: Nov. 27, 1989

[51] Int. Cl.$^5$ ............................................. C02F 1/22
[52] U.S. Cl. ...................................... 210/85; 210/86; 210/90; 210/746; 210/774; 210/806; 62/532; 62/540; 324/439
[58] Field of Search ............... 210/709, 710, 713, 741, 210/742, 746, 767, 768, 774, 806, 175, 85, 86, 90; 73/61 R, 61.1 R; 324/450, 138, 438, 439; 62/124, 532, 540

[56] References Cited

U.S. PATENT DOCUMENTS

| | | | |
|---|---|---|---|
| 2,340,721 | 7/1990 | Whitney | 62/540 |
| 3,838,774 | 7/1990 | Dolan et al. | 210/85 |
| 4,448,032 | 7/1990 | Hibino et al. | 52/124 |
| 4,496,906 | 7/1990 | Clack | 324/450 |
| 4,752,740 | 7/1990 | Steininger | 324/439 |
| 4,762,611 | 7/1990 | Schipper | 210/85 |
| 4,799,945 | 7/1990 | Chang | 62/124 |
| 4,849,098 | 7/1990 | Wilcock et al. | 210/85 |

Primary Examiner—Robert A. Dawson
Assistant Examiner—David Reifsnyder
Attorney, Agent, or Firm—Marvin Feldman

[57] ABSTRACT

A vessel is provided with a flexible plastic tube containing an electrical contact switch. Impure water is added to the vessel between the tube and the wall of the vessel. The vessel is then placed in a home freezer. Upon partial freezing of the impure water, the ice expands to flex or compress the tube to close the switch so as to actuate a detector or alarm. The user then removes the unfrozen water, and allows a fraction of the ice to melt. The just formed water is checked for purity by a conductivity measurement. If impure, the water is removed, and the ice is allowed to further melt until the desired purity level is reached at which time the remaining ice is melted to obtain purified water. The device and method are particularly suitable for home use to economically obtain purified water.

19 Claims, 2 Drawing Sheets

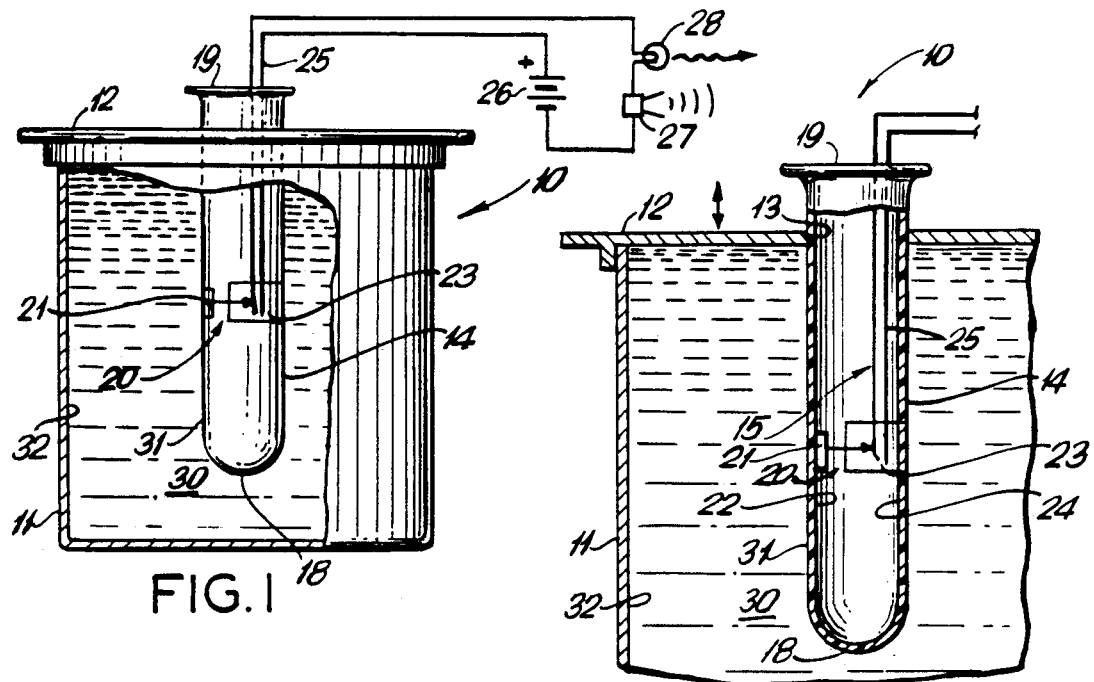
FIG.1
FIG.2
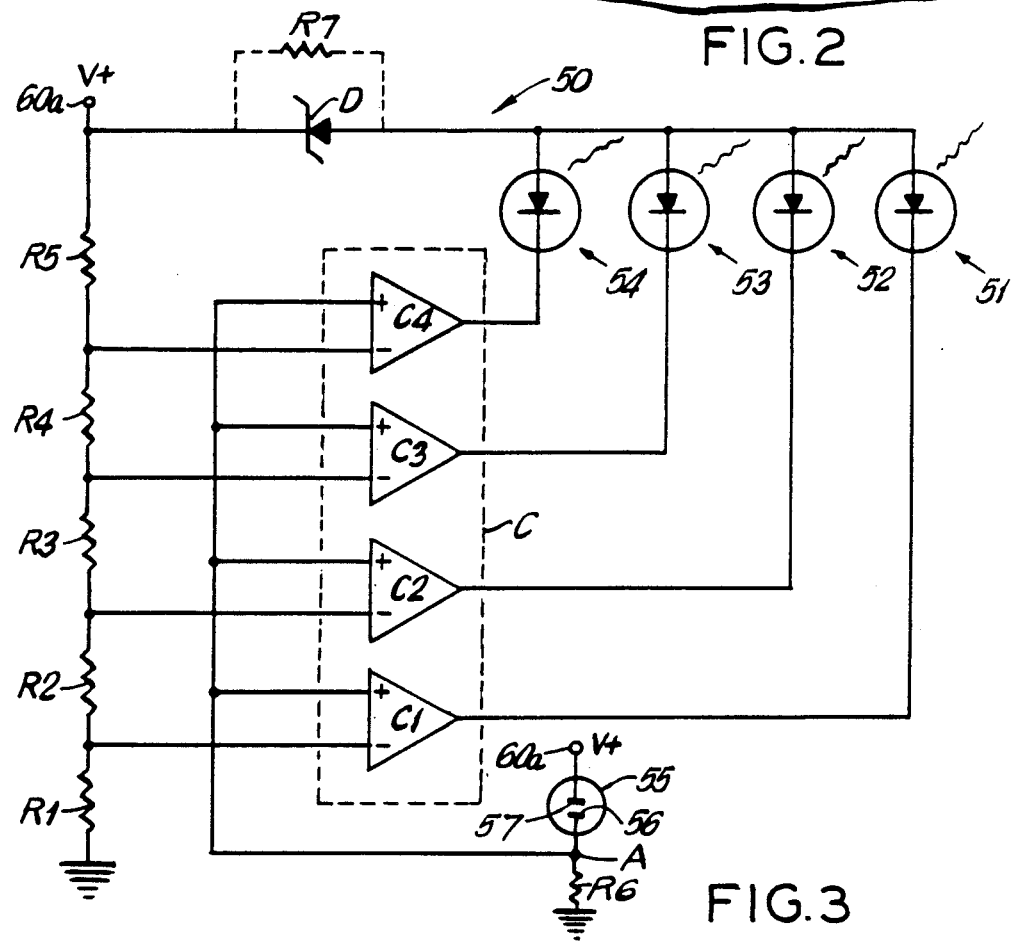
FIG.3

WATER PURIFICATION DEVICE AND METHOD

FIELD OF THE INVENTION

This invention relates to the making of fresh or pure water free of contaminants.

BACKGROUND OF THE INVENTION

The diminishing availability of water that is fit for consumption by humans has become a world-wide problem in the last decade. Industrial wastes and household chemicals, as well as leachates from cesspools and septic tanks are finding their way into the aquifers and surface water supplies. People are alarmed by reports of carcinogens and heavy metals, such as lead, cadmium, and the like, in their water.

Many people having lost confidence in the purity of their daily water supply, have chosen alternate supplies of drinking water. These water supplies are obtained by activated carbon filtering, reverse osmosis systems, distillation, and bottled water originating from diverse sources.

Each of these supplies has some disadvantages which are briefly summarized as follows:

Activated carbon filtering removes only organic contaminants and does not remove lead, sodium, nitrates, and the like. Also, the carbon chamber can become a breeding ground for bacteria which find their way into the so-called purified water, and may be harmful. The activated carbon filters must be replaced periodically.

Reverse osmosis systems are expensive to purchase, are energy intensive to operate, and require periodic replacement of expensive components.

Distillation systems are expensive to purchase, expensive to operate, and the heating source must eventually be replaced.

Bottled water is inconvenient and heavy to carry home from the store, and is costly to purchase over a period of time. There is also no guarantee that the quality of the water is that which the user desires and is in fact an improvement over tap water or other readily available water.

Various attempts have been made to purify water by freezing or partial freezing, such as are disclosed U.S. Pat. No. 2,340,721, granted Feb. 1, 1944 to Whitney; U.S. Pat. No. 4,448,032, granted May 15, 1984 to Hibino et al; and U.S. Pat. No. 4,799,945, granted Jan. 24, 1989 to Chang. These systems were complex and costly so as to militate against home use.

It was also known to measure the purity of water by conductivity determinations and other means, such as is disclosed in U.S. Pat. No. 4,762,611, granted Aug. 9, 1988 to Schipper; U.S. Pat. No. 4,496,906, granted Jan. 29, 1985 to Clack; U.S. Pat. No. 3,838,774, granted Oct. 1, 1974 to Dolan etal; and U.S. Pat. No. 4,752,740, granted June 21, 1988 to Steiminger. These systems did not however lend themselves to home use by a lay person.

With the increasing popular demand and need for pure water in the home, it was desired to provide a low cost and yet efficient device and method for obtaining purified water from impure water. There is now provided by the present invention a low cost device which is readily operated by a lay person and which provides purified water from tap water by a partial freezing method utilizing the home freezer.

SUMMARY OF THE INVENTION

The foregoing objectives are achieved by providing a vessel for receiving impure water with a member disposed in the vessel, such that upon partial freezing of the water in a home freezer or other convenient sub-freezing environment, the ice expands to cause the member to compress to close a switch to actuate an alarm or indicator so as to alert the user that a desired level of partial freezing has occurred. The user then removes the unfrozen water from the vessel, and allows ice to melt. The just formed water is analyzed by a conductivity meter of specialized design, to determine the water purity. Integral to this method is an electronic water quality meter which allows the operator to know when to perform a significant step in the procedure, namely, whether to discard the melt water, and to additionally determine if the method was performed properly so that the desired degree of purification of the final product was obtained. If the purity level is not that which is desired, the water is removed and ice is allowed to melt, and the conductivity measurement repeated, until the desired purity is achieved, at which time, all the ice is melted to obtain a volume of purified water.

In another aspect, the present invention is a specialized conductivity meter particularly useful in achieving this home use water purification.

In still another aspect, the present invention is a device as described above in which the partial freezing detecting member and water purity detection device are operated in a simple efficient manner for ready use in the home.

The partial freezing detecting member is a flexible or compressible plastic tube closed at its lower end, and containing an electrical contact switch which is normally open. The switch is electrically connected to an indicator or alarm. The tube is placed in the vessel, and the vessel filled with impure water between the outside of the tube and the inside wall of the vessel. Alternatively the impure water may first be added to the vessel and the tube then placed in the vessel. The vessel is then placed in a home freezer, and upon partial freezing, the ice expands to compress the tube to actuate the switch to set off the indicator or alarm. The user is alerted to the fact that partial freezing has occured and then removes the unfrozen impure water. The user then allows a small portion of the ice to melt. This portion of melt water is tested by a conductivity meter to determine the purity, and if not sufficiently pure, the water is removed, and a portion or fraction of the ice is allowed to melt and then retested for purity. This procedure is continued until purified water is obtained, and all the residue ice is allowed to melt.

BRIEF DESCRIPTION OF THE DRAWINGS

FIG. 1 is a sectional elevational view of one embodiment of the invention;

FIG. 2 is a detailed view of the embodiment of FIG. 1;

FIG. 3 is a schematic view of the water purity analyzer or conductivity meter to be used in conjunction with FIG. 1;

DESCRIPTION OF THE PREFERRED EMBODIMENTS

Figure 4:
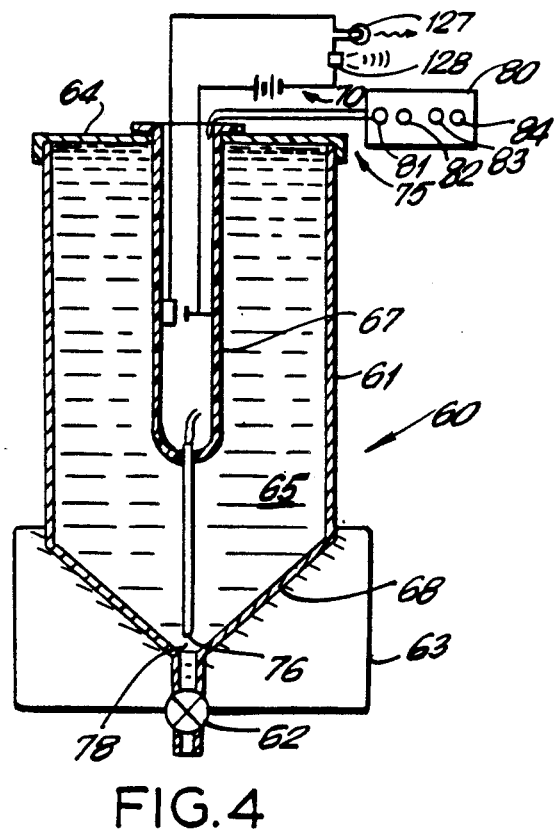
FIG. 4 is a sectional elevational view of another embodiment of the invention, at the start of the purifying method.

Referring to FIGS. 1-3 there is shown one embodiment of the present invention 10. Device 10 is, in general terms, composed of vessel 11, cover 12 having hole 13, plastic tube 14 removably receivable in hole 13, freezing determination assembly 15 in operable combination with tube 14, and water purity conductivity meter 50 (FIG. 3). Vessel 11 may be of any desired configuration and is composed of inert material so as not to contaminate the water. Tube 14 is of cylindrical shape having closed end 18 and open end 19. Tube 14 is preferably formed of food grade plastic. In addition, tube 14 is more flexible or compressible than vessel 11, for purposes hereinafter appearing.

Assembly 15 is formed of electrical contact switch 20, which has one electrical contact 21 mounted to one inside portion 22 of tube 14, while the opposed contact 23 is mounted to opposed inside portion 24. Contacts 21 and 23 are electrically connected, in series, through wire 25 to battery or power source 26, audible alarm 27 and visual indicator 28. When wall portions 22 and 24 are compressed, contacts 21 and 23 are contacted and the circuit of assembly 15 is closed to actuate alarm 27 and indicator 28.

Referring to FIG. 1, the vessel 11 is shown filled with water 30 disposed between the outside 31 of tube 14 and the inside 32 of vessel 11. Cover 12 is designed to hold the water in place so that with freezing the ice expand and preferably compresses tube 14 as opposed to raising cover 12 or outwardly expanding vessel 11. Vessel 11 and tube 14 may be designed so that with a degree of partial freezing, tube 14 compresses and the alarm and indicator are actuated to alert the user to the partial freezing.

The conductivity meter 50 of the present invention responds only to a relatively small range in the conductivity spectrum of water. This spectrum goes from greater than 45,000 micromhos for sea water to a maximum of 700 micromhos for potable water to 300 micromhos for typical well water. The conductivity meter of the present invention responds only to the range of from about 20 micromhos to 5 micromohs which is the conductivity range of the pure water produced by the present invention.

The meter of the present invention is not of conventional electro-mechanical design with a moving needle. This is so because at the high sensitivities required by the present invention, these conventional devices are very fragile and easily damaged.

Referring now to FIG. 3, the conductivity meter 50 of the present the invention uses several light emitting diodes 51, 52, 53, and 54 to indicate the quality of the pure water. When the water is sufficiently pure, the first diode 54 glows thus indicating that the water has reached the first level of acceptability. As the melting process continues, a second light emitting diode 53 will glow (i.e. 2 lights on) indicating increased purity. Continuing, a third light 52 comes on (i.e. 3 lights on) and finally, if the highest desired level of purity can be reached, a fourth light 51 comes on (i.e. 4 lights on).

This invention, therefore, allows a non-technical operator to readily observe small changes in conductivity and to clearly relate those changes to the purity level being achieved.

The meter circuit employs a sample cup 55 which has two cylindrical, parallel electrodes 56 and 57 with a space between. The water to be examined is poured into or received in the cup. Current now can flow from a battery or other power source 60a (V+) to one electrode, into and through the water to the other electrode, then through a resistor R6 to ground. As the impurity level of the sample decreases, the conductivity of the liquid decreases, allowing less current to flow through the circuit, causing the voltage at point A to decrease. Conversely, if the impurity level of the liquid rises, the conductivity increases allowing more current to flow through the circuit, and thereby causing the voltage at point A to increase.

The voltage at point A is conveyed to all of the positive inputs (non-inverting) of the comparator C. The negative (inverting) inputs of the comparator are connected in a sequential manner to a voltage divider consisting of five resistors R1-R5 connected in series between a power source 60a and ground. Therefore, the junction between the resistor R1 that has one of its leads grounded, and the next resistor in series with it is connected to the negative input of the first comparator C1. Accordingly, the junction between this latter resistor R2 and the next one in series with it, namely R3, is connected to the negative input of the second comparator C2 and so on. The resistance values of these resistors create a constant voltage at each of these four junctions, and measuring from ground, each junction will have a higher voltage than the preceding one closer to ground.

With the cup empty no current can flow through the R6 resistor since it is an open circuit and therefore the voltage at point A and the positive input of the comparators will be zero. The voltage at the negative inputs will be positive with respect to ground or point A as a result of the flow of current through the 5 resistor voltage divider. These are the reference voltages. Under these conditions, the comparator output will assume a logic low state approximating ground. The circuit conveys the output of the comparator to the cathodes of the LEDs, causing all the LEDs to be forward biased and thereby in a conducting state causing the emission of visible light from them. If very pure water is placed into or is received in the sample cup, the voltage at point A will rise, but not high enough to reverse the voltage across the comparators. As the purity of the sample decreases, the voltage polarity at point A will eventually rise higher than the first reference voltage at the negative input of comparator C1 and then the output of comparator C1 will change to a high logic state. This will reverse bias the LED wired to C1 causing it to cease to conduct current and extinguish the light output. The logic state of C2, C3 and C4 will not change yet, 3 lights will still be on.

The resistance valves for R1, R2, R3, R4 and R5 are 5.1K ohms, 3.3K ohms, 3.3K ohms, 3.3K ohms and 62K ohms, respectively. Comparator C may be a LM339 quad comparator.

As the impurity level of a new sample increases, the voltage at A will continue to increase eventually rising higher than the reference voltage at C2 causing that output to change state and extinguish its associated LED. It can be seen that following this pattern, eventually all of the LEDs will turn off, indicating that the water is no longer in the acceptable pure range. Zener diode D, or alternatively a limiting resistor R7 (1K ohm), limits the current through the LEDs to a safe level and completes the circuit. R7 is shown as an alternative element in broken line in FIG. 3.

Figure 5:
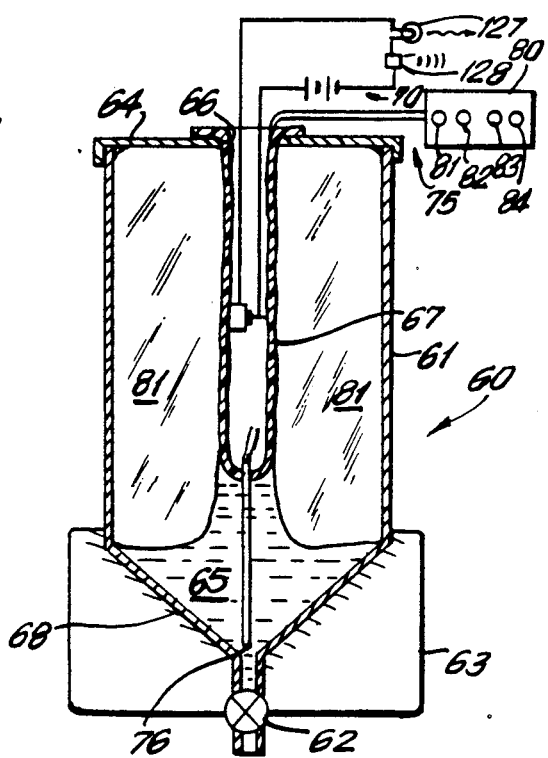
FIG. 5 is a sectional elevational view of the embodiment of FIG. 4, after a pre-determined level of freezing is achieved.
Figure 6:
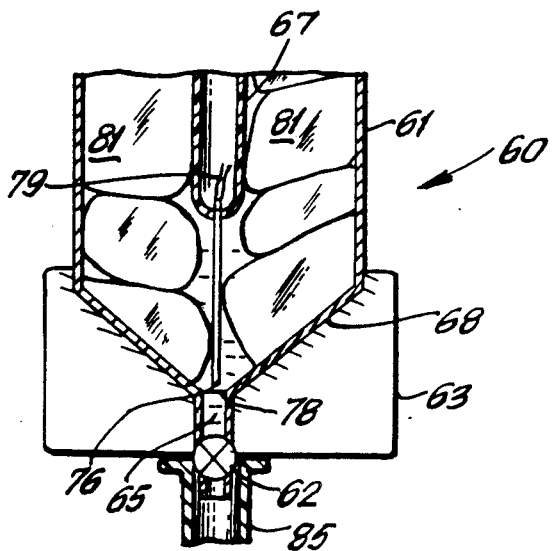
FIG. 6 is a partial sectional view of the embodiment of FIG. 4, after the desired level of water purity is achieved.

Referring to FIGS. 4-6, There is shown an embodiment of the invention 60. Device 60 is formed of vessel 61 having rigid walls 60 with tapered bottom portion 68, discharge valve 62 and support base 63. Cover 64 is provided to tightly enclose water sample 65 in vessel 61, and cover 64 is provided with hole 66 to receive tube 67.

A partial freezing determination device 70 is shown disposed in flexible plastic tube 67. Device 70 is similar to device 15 as hereinbefore described having audio alarm 128 and visual indicator 127. Tube 67 is similar in design and construction to tube 14 hereinbefore described. A conductivity meter 75 is of similar design to that of meter 50, except that it is operably combined with tube 67 and vessel 61. Specifically, sample cup 76 is disposed at the end of tube 67, and is disposed adjacent the bottom 78 of vessel 61. The wires 79 connect the electrodes of sample cup 76 with the operative electronic components in housing 80. The four LED's 81-84 indicate the different purity levels in a manner as previously described in connection with the embodiment of FIGS. 1-3.

In this manner of construction, device 60 is operated by the user filling vessel 61 with water 65, with valve 62 closed. The cover 64 then tightly encloses vessel 61. The user then inserts tube 67 with freezing determination device 70 and conductivity meter 75 (FIG. 4). The user then places the device 60 in a home freezer. Upon partial freezing, ice 81 expands to compress tube 67 and actuate the freezing determination device as aforediscussed. Alarm 128 signals the user (FIG. 5). The user removes the device from the freezer. The user then opens valve 62 and allows the unfrozen impure water to flow out of the vessel. Valve 62 is then closed. The user then allows ice to melt until the melt water causes one or more of the LED's 81-84 to light, indicating the desired level of purity. The user has the option of discarding the melt water if not at the desired purity level. When the desired purity is reached, the user allows the remaining ice to melt, and places a clean collection vessel or plastic container 85 under valve 62, opens valve 62 and allows the pure water to be collected in container 85. The user can also readily monitor the water purity as it is being collected to assure the desired purity level of the collected water.

The following example illustrates the method of the invention in conjunction with the embodiment of FIGS. 1-3.

EXAMPLE

1. The container or vessel is filled with the sample of water to be purified.
2. The insert tube or member is positioned in the vessel, with the cover holding the tube in the vessel thereby enclosing the sample.
3. The container is placed in a freezer compartment of a home freezer.
4. When the tube member indicator is activated, the container is removed from the freezer environment. The insert tube is removed and the liquid (unfrozen) portion is poured off.
5. Some melting of the ice is allowed to occur and the melt water is tested with the electronic water quality tester or conductivity meter.
6. If the first (lowest purity) indicator lights, the rest of the ice is allowed to melt. Step No. 8 is then followed.
7. If no indicator lights, the accumulated melt water is poured off and another small quantity of melt water is allowed to accumulate. The new melt water is tested, and this step is repeated until the first indicator lights. When the first indicator lights, the remaining ice is allowed to melt.
8. When only a small amount of ice remains, the melt water is again tested to re-determine the quality of purified water produced.

It is important to note that with 1 or 2 indicator lights on, the water has less impurities than any tap water or bottled water. A level of 3 indicator lights on is readily achieved by the present invention and indicates very pure water. A level of 4 indicator lights denotes water with 95% to 99% or more of the impurities removed.

The tube of the present mention, in addition to the aforesaid functions, aids in the partial freezing by providing additional surface for freezing; allows the cold air to flow on the inside of the tube; prevents the vessel from rupturing; is removable to allow ice to melt and keeps contaminents out of the vessel. It is also to be noted that in allowing the ice to partially melt, the water impurities concentrate at the ice surface and thus on melting the impurities are in the melt water to be discarded.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

What is claimed is:

1. A water purifying device comprising, a vessel for containing water to be purified; means disposed in operative relationship with said vessel for indicating an extent of partial freezing of said water; and means for determining the purity of the water; whereby after partial freezing, the water is removed from the vessel, and the ice allowed to partially melt and the melt water subjected to a purity determination by said means, and if the melt water is impure, it is discard, and the ice allowed to further partially melt until the desired purity is determined and when the desired purity level is reached the remaining ice is melted to provide purified water.

2. The device of claim 1, wherein the means for determining the extent of freezing comprises a flexible member, and switch means operably disposed with said member, and indicator means and power supply means operably connected to said switch means, whereby with partial freezing the ice expands in the vessel to flex the member and close the switch means to actuate the indicator means so as to indicate that a certain level of partial freezing has occurred.

3. The device of claim 2, said member comprising a tube closed at an end and said end being disposed in said vessel.

4. The device of claim 3, said tube being removable from the vessel.

5. The device of claim 3, wherein the means for determining the freezing and the means for determining the purity are operably disposed in said member.

6. The device of claim 2, said member being formed so as to be compressed by the ice in the vessel.

7. The device of claim 2, wherein the member is more flexible than the vessel.

8. The device of claim 1, said means for determining the purity of the water comprising a conductivity meter.

9. The device of claim 8, said conductivity meter comprising means for receiving a sample of water to be tested; means for determining a range of only about 20 micromhos to 5 micromhos conductivity of the water; and means for indicating a plurality of conductivity levels in said range; and power source means being operably connected to said conductivity range determining means and said indicating means, whereby when each of said conductivity levels is in turn reached the respective indicating means is actuated to indicate same.

10. A method of purifying water comprising;
    (a) filling a vessel with impure water;
    (b) partially freezing the water;
    (c) determining the extent of the partial freezing of the water;
    (d) removing the unfrozen water from the ice;
    (e) allowing a portion the ice to melt;
    (f) detecting the purity level of the melt water from step (e); discarding the melt water if not at the desired purity level, and repeating steps (e) and (f) and when the purity level of the water is at an acceptable level, allowing the remaining ice to melt to obtain purified water.

11. The method of claim 10, wherein the partial freezing is in a home freezer.

12. The method of claim 10, further including and means for determining partial freezing including a flexible member, so that upon said partial freezing, the ice expands to flex the member to actuate the means to determine that said partial freezing has occured.

13. The method of claim 10, wherein the detecting of the purity level is by water conductivity determining means.

14. The method of claim 8, wherein step (b) further comprises inserting said means in said vessel.

15. A water purity meter comprising; means for receiving a sample of water to be tested; means for selectively determining a range of only about 20 micromhos to 5 micromhos conductivity of the water; and means for indicating two or more of a plurality of progressively decreasing respective specific conductivity levels within said range; and power source means being operably connected to said conductivity range determining means and said indicating means, whereby when in turn each of said decreasing conductivity levels is measured, the respective indicating means is in turn actuated to indicate same, so that an operator of limited skill can determine the desired specific level of water purity.

16. The meter of claim 15 wherein said indicating means comprises a plurality of independently actuable LEDs.

17. The meter of claim 15, a flexible member and means for operably connecting said flexible member to said conductivity level determining means, whereby on partial freezing of said water sample, said member flexes and the conductivity of the unfrozen water or melt water sample is determined.

18. The meter of claim 15, said means for receiving a water sample being formed to receive one sample, so that the conductivity levels are measured from a melt water portion or an unfrozen portion of the sample.

19. The meter of claim 15, said indicating means comprising 3 or more indicating means.

* * * * *